United States Patent [19]

Weisblum

[11] 4,376,823

[45] Mar. 15, 1983

[54] METHOD OF INCREASING THE ANTIBIOTIC YIELD OF PRODUCING ORGANISMS

[75] Inventor: Bernard Weisblum, Madison, Wis.

[73] Assignee: Wisconsin Alumni Research Foundation, Madison, Wis.

[21] Appl. No.: 274,728

[22] Filed: Jun. 18, 1981

[51] Int. Cl.$^3$ .................... C12P 19/62; C12P 19/64; C12N 15/00; C12R 1/29; C12R 1/365; C12R 1/465; C12R 1/54; C12R 1/565

[52] U.S. Cl. ........................................ 435/73; 435/76; 435/172; 435/867; 435/872; 435/886; 435/900; 435/896

[58] Field of Search .................... 435/73, 76, 872, 172, 435/896, 900, 886, 244, 867

[56] References Cited

PUBLICATIONS

Fujisawa et al., J. Bacteriol., 146(2), 621-631 (May 1981).
Metzler, Biochemistry-The Chemical Reactions of Living Cells, Academic Press, Inc., New York, 908 (1977).
Weisblum et al., J. Bacteriol., 106(3), 835-847 (1971).
Weisblum et al., J. Bacteriol., 137(1), 635-643 (1979).
Graham et al., J. Bacteriol., 137(3), 1464-1467 (1979).
Weisblum et al., J. Bacteriol., 138(3), 990-998 (1979).

Primary Examiner—Esther M. Kepplinger
Attorney, Agent, or Firm—Quarles & Brady

[57] ABSTRACT

A method of increasing the yield of a desired product, such as an antibiotic, by an organism which normally must first become inducibly resistant to that product before it can produce the product in maximum yields comprises producing constitutively resistant cells of the organism by supplementing a culture of the organism with an agent in which only cells able to specifically modify the 23S ribosomal RNA constitutively, rather than inducibly, survive thereby producing an organism in which the resistance to the product is expressed without the need for activation by the induction process; followed by purification and utilization of that organism for increased product production.

10 Claims, No Drawings

METHOD OF INCREASING THE ANTIBIOTIC YIELD OF PRODUCING ORGANISMS

The Government has rights in this invention pursuant to Grant No. PCM-7719390 and IPA No. 0001 awarded by the National Science Foundation.

FIELD OF THE INVENTION

The present invention relates to a novel method of increasing the antibiotic yield of antibiotic producing organisms which must first become resistant to the antibiotics they produce before producing these antibiotics in maximum yield.

BACKGROUND OF THE INVENTION

It is known that certain organisms that produce antibiotics have internal protective mechanisms that make them resistant to the antibiotic which they produce. The production of antibiotics by such organisms appears to be characterized by a "lag period" caused by the requirement of the organisms to first become resistant to the antibiotics they produce prior to initiating antibiotic synthesis. As a result, the synthesis of the desired antibiotics in useful amounts is delayed.

In the case of *Streptomyces lincolnensis* and *Streptomyces fradiae*, organisms that product lincomycin and tylosin, respectively, resistance to these antibiotics appears to be of the inducible form. It thus appears that for the organisms to remain viable while synthesizing their respective antibiotics, they must somehow express resistance to the antibiotics they produce. Several models may account for the induction—e.g. (i) production of low, subinhibitory levels of antibiotic may induce resistance in the cell prior to initiation of full-scale antibiotic production, or (ii) production of a potent endogenous inducer which may enable full-scale antibiotic production after the producing cells have become maximally induced.

A method of increasing the antibiotic yield of antibiotic producing organisms which first must become inducibly resistant before producing the antibiotic in useful amounts by eliminating the "lag period" required for the organisms to become inducibly resistant obviously would be valuable.

SUMMARY OF THE INVENTION

It is the primary object of the present invention to disclose a method of increasing the antibiotic production of an antibiotic producing organism which must be inducibly resistant to the antibiotic which it produces by eliminating the "lag period" and thereby increasing the efficiency and antibiotic output of the organism.

The inventive method of the present invention eliminates the "lag period" and thus increases the antibiotic yield of the antibiotic producing organism by producing constitutively resistant cells of the organism in which resistance to the antibiotic is expressed without the need for activation by the induction process.

The method of the present invention comprises supplementing a culture of the antibiotic producing organism with an agent which will select mutant cells able to specifically methylate the 23S ribosomal RNA without the need for an inductive stimulus (constitutive mutants), then selecting, purifying and using those constitutively resistant organisms for more efficient antibiotic production.

In one specific embodiment of the invention, selection applied to a *S. fradiae* culture by addition of erythyromycin produces constitutively resistant cells that produced higher yields of tylosin without a "lag period". In another embodiment, the practice of the inventive method employing *S. lincolnensis* as the producing organism and maridamycin as the selecting agent produces constitutively resistant cells that are more efficient producers of lincomycin.

DESCRIPTION OF THE PREFERRED EMBODIMENT

In the preferred embodiment, the antibiotic producing organism is a member of the Streptomyces family and the agent with which the culture of the organism is selected is an antibiotic with low inducing activity selected from amongst three chemically dissimilar classes of antibiotics which inhibit 50S ribosome subunit function—the macrolides, lincosamides, and streptogramin type B antibiotics (hereafter referred to collectively as the "MLS" antibiotics).

The rationable for the use of MLS antibiotics with low inducing activity is based on the finding that inducible cells inoculated into medium containing a high concentration of an inducing MLS antibiotic eventually grow as a consequence of becoming (phenotypically) induced in situ, not by mutation. In contrast, the probability of induction in situ is markedly reduced if the MLS antibiotic used for selection has low inducing activity but normal inhibitory activity, so that cells selected by the procedure have a higher probability of being constitutive mutants, a fact which can be demonstrated experimentally.

Cells selected by this method can be recognized by the acquisition of co-resistance to other MLS antibiotics or by an alteration in the pattern or level of adenine methylation in their 23S ribosomal RNA. In the case of *S. fradiae* and *S. lincolnensis* this type of selection has resulted in the isolation of mutant strains with increased production of tylosin and lincomycin respectively, as manifested in assays of inhibitory activity of the fermentation broth on each of 5 successive days.

The following experimental work demonstrates that in both inducibly resistant cells and constitutively resistant cells the 23S ribosomal RNA a structural component of the 50S ribosomal subunit (the target of the MLS antibiotics) has an increased level of methylation (over uninduced inducible controls) and that constitutively resistant mutant cells may be prepared by the practice of the method of the invention.

EXPERIMENTAL

MATERIALS AND METHODS

Bacterial strains. *S. viridochromogens* NRRL 2860, provided by J. C. Ensign, who has described the properties of this organism in a review (Annu. Rev. Microbiol. 32: 185–219, 1978.), was grown in enriched medium containing (per liter) 5 g of yeast extract (Difco) and 5 g of tryptone (Difco). *Streptomyces hygroscopicus* IFO 12995, a producer of the macrolide antibiotic maridomycin, was obtained from the collection of the Takeda Co. The remaining Streptomyces strains were cultures which have been placed on permanent deposit with the culture collection of the Northern Regional Research Laboratories, North Utilization Research and Development Division, Agricultural Research Service, U.S. Department of Agriculture, Peoria, Illinois, and assigned NRRL accession number.

Determination of resistance on solid medium. Mycelial suspensions of cells grown in enriched-medium were disrupted by sonic oscillation for 10 seconds to obtain a homogeneous suspension for preparation of pour plates by the agar overlay method. The disks used to determine resistance contained 20 μg of test antibiotic.

Induction studies. To test induction in liquid medium, a sonicated cell suspension containing $10^6$ colony-forming units per ml suspended in growth medium was incubated under the conditions of time and inducer concentration described. The induction medium was sampled, and suitable dilutions were plated onto medium containing 50 μg of tylosin per ml to determine the concentration of induced colony-forming units in the medium, and onto antibiotic-free medium to determine the total viable colony-forming units.

Selection of constitutively resistant mutants. For selecting mutants, MLS antibiotics producing large clear inhibition zones were used. The rationale behind this choice was that MLS antibiotics showing small inhibition zones would probably induce in situ, and selection using such antibiotics would have a high probability of inducing the culture rather than selecting desired constitutively resistant mutants.

Altered methylation of 23S rRNA. 23S rRNA was labeled with either [2-$^3$H]adenine or [methyl-$^{14}$C]methionine in the presence or absence of inducer, as required. Inocula were grown in enriched medium supplemented with 1 g of $K_2HPO_4$ and 2 g of glucose per liter. For labeling experiments, actively growing mycelia from 100 ml of enriched medium were collected by centrifugation and suspended in 100 ml of M-9 medium containing (per liter): $Na_2HPO_4$, 6 g; $HK_2PO_4$, 3 g; NaCl, 0.5 g; $NH_4Cl$, 1 g; 0.1 M $MgSO_4$, 10 ml; 0.01 M $CaCl_2$, 10 ml; and 50% glucose, 10 ml. The M-9 medium was additionally supplemented with 2% Casamino Acids and [$^3$H]adenine (specific activity, 15,000 Ci/mol; final concentration, 4 μCi/ml). Cells were labeled by incubation overnight (generally 14 to 18 h), collected, washed with 0.15 M NaCl solution, and stored at −20° C. until used. Cells were disrupted by sonic oscillation, and labeled 23S rRNA was purified from the 50S ribosome subunits (obtained by sucrose density gradient centrifugation) by extraction with phenol, followed by depurination and separation of the resultant purines by column chromatography on Dowex-50X8 and paper chromatography in an isopropanol-ammonia-water (85:1.3:15) system as previously described (Lai, C. J. and B. Weisblum Proc. Natl. Acad. Sci. U.S.A. 68: 856–860, 1971). To label cells with [methyl-$^{14}$C]methionine, enriched medium diluted fivefold with water and supplemented with methionine (specific activity, 50 Ci/mol, 0.1 μCi/ml) was used, methyl-$^{14}$C-labeled 23S rRNA was digested with RNase A, and the resultant digest was fractionated with DEAE paper by the two-dimensional method of Brownlee et al. J. Mol. Biol. 34: 379–412 (1968).

RESULTS

The requirements for induction were characterized by using *S. viridochromogenes*, as a model test system, because of the fact that this organism is not known to produce any MLS antibiotics, a factor that might tend to mask induction by exogenously added inducers. The disk sensitivity method was used initially for determination of induced-resistance specificity profiles.

Patterns of induction in *S. viridochromogenes*. The ability of tylosin to induce resistance to erythromycin and to carbomycin was manifested by the distorted erythromycin and carbomycin inhibition zones on the side facing the tylosin disk; the distorted inhibition zone resulted from the fact that cells induced on solid medium by tylosin, which diffuses from the disk, are capable of growing closer to the erythromycin or carbomycin disk, whereas the minimal inhibition zone surrounding the tylosin disk reflects the effectiveness of tylosin as inducer of resistance to itself.

We have shown previously that MLS antibiotics lacking inducing activity can be used to select constitutively resistant *S. aureus* mutants. A mutant of *S. viridochromogenes* selected for resistance to carbomycin shows coresistance to all remaining members of a test panel of MLS antibiotics consisting of erythromycin, carbomycin, tylosin, chalcomycin, cirramycin, clindamycin, maridomycin, ostreogrycin B, and kitasamycin. When wild-type inducible *S. aureus* was tested similarly for induction, it was noted that erythromycin induced resistance to tylosin, whereas neither carbomycin nor tylosin had demonstrable inducing activity (Tanaka. T., and B. Weisblum, Antimicrob. Agents Chemother. 5: 538–541, 1974). Thus it can be concluded that both *S. viridochromogenes* and *S. aureus* behave in a formally similar manner when tested for induction, but with differences in inducer specificity.

Requirements for induction in *S. viridochromogenes*. The process of induction in *S. viridochromogenes* has both a time and inducer concentration dependence. To obtain reproducible quantitative data, it was necessary to prepare a homogeneous cell suspension. Baltz in J. Gen. Microbiol. 107: 93–102 (1978) has shown that a 100-fold-increased level in the number of colony-forming units is obtained if a mycelial suspension of *Streptomyces fradiae* is disrupted by sonication for 5 to 10 seconds before plating, and this method was employed without modification. Under the conditions used, optimal induction, measured in terms of the appearance of colony-forming units, required exposure for 1 h to a concentration of tylosin in the range of 0.3 to 0.6 μg/ml.

Altered methylation of 23S rRNA in resistant cells. [methyl-$^{14}$C]methionine was used as the source of label, followed by digestion of the labeled 23S rRNA sample with RNase A, two-dimensional fractionation of the resultant digest, and autoradiography. Two additional spots in the rRNA from induced cells were seen: one distinctly labeled fragment in the lower part of the autoradiograph and a second, partially resolved spot in the upper part. No attempt was made to maximize the resolution of the larger, partially resolved fragment from its neighbors; however, the results suggest the possibility of at least two inducibly methylatable sites in 23S rRNA. The base compositions of these oligomers were not investigated further, but from our previous studies in *S. aureus* as reported in Lai, C. J. et al., Biochemistry 12: 457–460 (1973), we were able to locate the methylated adenine residue in a similar type of fragment.

Quantitative data are obtainable by labeling cells uniformly with [2-$^3$H]adenine, which allowed determination of the average number of adenine residues that were methylated. It is assumed that all adenine residues in 23S rRNA are labeled to the same average specific activity, and that the relative amount of each derivatized form of adenine present in 23S rRNA is reflected in the relative amount of radioactivity present in that component. Since 23S rRNA contains aproximately 800 adenine residues, one methylated adenine per 23S subunit would comprise 0.12% of the total adenine fraction. Results of such an assay, summarized in Table 1, indicate the presence of 0.13 and 0.17% monomethyl adenine relative to total adenine for the inducible and constitutively resistant strains, respectively.

Reduced erythromycin binding by resistant cells. 50S ribosome subunits from uninduced, induced, and constitutively resistant *S. viridochromogenes* were tested for their ability to bind erythromycin. The extent of association between erythromycin and 50S ribosome subunits was measured by adsorption of the complex to nitrocellulose membrane filters by a method which allows uncomplexed erythomycin to pass through the membrane filter unadsorbed. Results of the assay were similar to those obtained in previous studies of erythromycin binding by 50S subunits from uninduced, induced, and constitutively resistant *S. aureus*. It can be concluded that tylosin-inducible MLS resistance in *S. viridochromogenes* formally resembles erythromycin-inducible MLS resistance in *S. aureus* at the ribosome level.

Variety of MLS resistance phenotypes in Streptomyces spp. A group of selected Streptomyces strains were surveyed to determine whether additional specificities of induction might be present. Of several possible tests for induction, effort was concentrated on two: (i) the disk assay to determine specificity of induction, and (ii) the [$^3$H]adenine methylation assay, to determine the altered adenine methylation phenotype and to obtain an estimate of the number of altered sites. Results of the methylation assay are presented in tabular form. The strains chosen produce MLS antibiotics; however, as in the case of *S. viridochromogenes* and other examples cited, MLS resistance is not restricted in distribution to MLS producers and seems to occur in many Streptomyces strains that were tested. A wide range of phenotypes was found in the survey. Therefore the data below is presented in a form that illustrates the diversity encountered, rather than exhaustively documenting requirements for induction in all the samples.

Streptomyces lincolnensis NRRL 2936. Examination of the response of *S. lincolnensis* to antibiotic disks revealed the distorted inhibition zones characteristic of induction. Cirramycin induced resistance to carbomycin and (more distinctly) to maridomycin. A more pronounced flattening of the carbomycin inhibition zone in response to cirramycin was seen.

To demonstrate that a common mechanism was responsible for resistance to the several MLS antibiotics to which *S. lincolnensis* appears sensitive, a mycelial suspension of *S. lincolnenis* was inoculated into enriched growth medium supplemented with maridomycin, final concentration 10 μgm/ml. After 72–96 hours of growth at 32° C. a mutant selected with maridomycin was isolated, purified and tested. The mutant selected showed increased resistance to the previously described set of test MLS antibiotics. The mutant when assayed for inhibitory activity in fermentation broth demonstrated increased production of lincomycin without the "lag period" characteristic of inducibly resistant cells.

The presence of methyl adenine was checked in *S. lincolnensis* grown (i) in the absence of antibiotic, (ii) in the presence of an inducing concentration of lincomycin, and (iii) in the constitutively resistant strain selected with maridomycin. Results parallel to those obtained in *S. virodochromogenes* were observed, demonstrating that adenine methylation similarly mediates lincomycin resistance in *S. lincolnensis*.

*S. fradiae* NRRL 2702. Erythromycin induced resistance to the macrolide antibiotic lankamycin and to vernamycin B in *S. fradiae*. Examination of the response of *S. fradiae* to the test group of MLS antibiotics showed resistance to most of the members of this group with the exception of erythromycin and vernamycin B, to which it appeared to be sensitive. The absence of a significant inhibition zone for seven of the nine antibiotics tested can be interpreted to indicate a high level of inducing ability and a relatively lower level for the remaining two antibiotics tested, erythromycin and vernamycin B. Therefore, erythromycin also was used to select constitutively resistant mutants a strain with higher levels of resistance to both erythromycin and vernamycin B was obtained.

A constitutively resistant mutant strain of *S. fradiae* NRRL 2702 was obtained (by following the procedure described above for preparing a constitutively resistant mutant of *S. lincolnensis* utilizing maridomycin as the selecting agent) but using instead, erythromycin in a concentration of 10 μgm/ml as the selecting agent. The mutant when assayed for inhibitory activity in fermentation broth demonstrated increased tylosin production without the characteristic "lag period."

Examination of the methylation pattern in 23S rRNA revealed the presence of monomethyl adenine in the uninduced control, as in our previous study reported in J. Bacteriol. 137: 1464–1467 (1978), in which we also noted the presence of monomethyl adenine in 23S rRNA from *Streptomyces cirratus* ATCC 21731, an organism that produces the macrolide antibiotic cirramycin. In studying *S. fradiae* further, however, we made the unexpected observation that dimethyl adenine was the predominant methylated form present in the mutant selected with erythromycin. The apparent shift from mono- to dimethylation raises the question of whether one or two enzymes are responsible for the observed rRNA methylation patterns. The smaller zone diameter around the erythromycin disk seen in the erythromycin-resistant mutant is reminiscent of the partially constitutive mutants of *S. aureus* found in earlier studies, and this pattern of mutation can be interpreted to reflect a nucleotide change that only partially destabilizes the r-determinant control region for MLS resistance as described by Horinouchi and Weisblum in Proc. Natl. Acad. Sci. U.S.A. 77:7079–7083 (1980).

*S. hydroscopicus* IFO 12995. In testing the specificity of induction it was found that either of the two streptogramin B antibiotics, vernamycin B and ostreogrycin B, induced resistance to erythromycin. This observation is noteworthy since it represents that induction can be achieved by a member of the streptogramin B family. Erythromycin was used in an attempt to select constitutively resistant mutants, and the strain obtained in this way became coresistant to the remaining members of the test group.

Equimolar concentrations of mono- and di-methyl adenine were found in 23S rRNA from both the uninduced control and the constitutively resistant mutant. Whereas rRNA from uninduced *S. hydroscopicus* conformed to the pattern of methylation found for other macrolide producers, namely, the presence of monomethyl adenine, the simultaneous presence of dimethyl adenine provides an additional variant methylation phenotype, possibly due to the presence of two methylating enzymes. It is felt that macrolide-producing strains may synthesize their own inducers and that this may account for the observed presence of methylated adenine in macrolide-producing strains apparently unrelated to induction by exogenously added inducer.

*Streptomyces diastaticus* NRRL 2560. Cirramycin clearly induced resistance in *S. diastaticus* to kitasamycin and maridomycin. The same disk assay did not show induction by a streptogramin B-type antibiotic, however, in view of a relatively small inhibition zone observed surrounding the vernamycin B disk, it was inferred that vernamycin B might nevertheless have inducing activity, and it was used in the assay of induced methylation. The results suggested the apparent induction of a low level of dimethyl adenine formation which remains to be optimized. This observation is of interest since it provides an additional example of induction in a producing organism by an antibiotic produced by that organism. Moreover, these results further suggest the existence of inducing activity in a streptogramin B-type antibiotic.

Other *Streptomyces spp.* By means of the disk method additional Streptomyces strains were examined which were specifically chosen because of their role in the synthesis of antibiotics that do not belong to the MLS families. Examination of *Streptomyces rimosus* NRRL 2234 and *Streptomyces griseus* NRRL B-1965, the organisms used to synthesize oxytetracycline and streptomycin, respectively, revealed that chalcomycin induces resistance to maridomycin in both these strains.

These findings prompt a redefinition of the MLS phenotype in terms of the fact that macrolides, lincosamides, and streptogramin B-type antibiotics can all induce resistance, and that the induced ribosomal alteration involves either mono- or dimethylation or both. This broader definition of the inducible MLS resistance phenotype subsumes all the variant phenotypes found to date.

The studies reported above were originally undertaken to determine whether a causal relation could be shown between adenine monomethylation and MLS resistance. The use of an inducible strain, *S. viridochromogenes*, one not known to produce MLS antibiotics, provided the model system that enabled this to be done with equal facility as in *S. aureus*. To prove, however, that an organism does not synthesize compounds with inducing activity may be difficult, so that the use of a strain not known to produce any MLS antibiotics is the optimal choice at this time.

*S. viridochromogenes* provided an additional example of induction specificity in which erythromycin was not the most potent inducer. It had been previously shown that erythromycin was not the sole inducer in staphylococci and streptococci. Although erythromycin has maximal inducing activity in certain cases, this did not appear to be the case universally after examination of the Streptomyces spp.

In the course of the studies of MLS resistance we faced the problem of explaining the basis for induction specificity. In studies of a series of 53 erythromycin analogs by Pestka et al. reported in Antimicrob. Agents Chemother. 9: 128-130 (1976) a correlation between ribosome binding and inducing activity was noted, and they inferred that formation of a ribosome-erythromycin complex constituted a significant step in induction. More recent studies of MLS resistance by Shivakumar et al. reported in Proc. Natl. Acad. Sci. U.S.A. 77: 3903-3907 (1980) and from our laboratory Proc. Natl. Acad. Sci. U.S.A. 77: 7079-7083 (1980) have suggested that the process of induction requires sensitive ribosomes and that formation of a complex between erythromycin and a sensitive ribosome plays a key role in the induction process.

On the basis of the DNA sequence of the control region for inducible resistance specified by plasmid pE194 from *Straphylococcus aureus,* including sequences of 11 constitutive mutants, an explicit translational attenuation model for induction of MLS resistance was proposed which is believed to be utilized in regulating MLS resistance in Streptomyces spp. as well (Horinouchi, S. and B. Weisblum, Proc. Nat. Acad. Sci. supra.). The significant feature of the model of induction pertinent to the present invention is the experimental fact that members belonging to the three classes of antibiotics to which methylated ribosomes are resistant can, in principle, show inducing activity.

In the case of the MLS antibiotic producers, the presence of methylated adenine was found in cells grown under noninducing conditions (i.e., in the absence of exogenously added inducer) and apparent inducibility of these strains when tested by the disk method. In the case of *S. lincolnensis,* it was found that the ribosomes lack methylated adenine until exposed to exogenously added lincomycin. It appears that under conditions used for antibiotic production, lincomycin or some congener such as celesticetin, produced initially at subinhibitory levels, may serve to mediate the metabolic switch that occurs as part of the commitment to antibiotic production.

TABLE 1

METHYLATED ADENINE RESIDUES IN 23S rRNA

| Species | cpm in adenine | cpm in monomethyl adenine (% relative to adenine) | cpm in dimethyl adenine (% relative to adenine) |
|---|---|---|---|
| *S. viridochromogenes* | 826,000 | 276(0.03) | 243(0.03) |
| Tylosin induced | 554,000 | <u>740(0.13)</u> | 283(0.05) |
| Carbomycin resistant | 581,000 | <u>984(0.17)</u> | 208(0.04) |
| *S. lincolnensis* | 380,000 | 211(0.05) | 198(0.05) |
| Lincomycin induced | 867,000 | <u>642(0.07)</u> | 247(0.03) |
| Maridomycin resistant | 426,000 | <u>844(0.20)</u> | 168(0.04) |
| *S. fradiae* | 232,000 | <u>522(0.23)</u> | 195(0.08) |
| Erythromycin resistant | 579,000 | 386(0.06) | <u>949(0.16)</u> |
| *S. hygroscopicus* | 575,000 | <u>994(0.17)</u> | <u>1367(0.24)</u> |
| Erythromycin resistant | 153,000 | <u>513(0.34)</u> | <u>494(0.32)</u> |

[a]Adenine and its methylated derivatives were isolated from 23S rRNA as described. Radioactivity (counts per minute, cpm) in each of the methylated adenine fractions was determined, and the results were tabulated; 0.12% relative to adenine corresponds to 1 residue per 23S. Underlined data indicate experimental values corresponding to one or more methylated adenine residues per 23S ribosomal RNA.

From the foregoing experimental work, it is clear that inducible resistance to macrolide, lincosamide, and streptogramin type B antibiotics in Streptomyces spp. comprises a family of diverse phenotypes in which characteristic subsets of the macrolide-lincosamide streptogramin antibiotics induce resistance mediated by mono- or dimethylation of adenine, or both, in 23S ribosomal ribonucleic acid. Diverse patterns of induction specificity in Streptomyces and associated ribosomal ribonucleic acid changes were described above. In *Streptomyces fradiae* NRRL 2702 erythromycin induced resistance to vernamycin B, whereas in *Streptomyces hygroscopicus* IFO 12995, the reverse was found: vernamycin B induced resistance to erythromycin. In a *Streptomyces viridochromogenes* (NRRL 2860) model system studied in detail, tylosin induced resistance to erythromycin associated with $N^6$-monomethylation of 23S ribosomal ribonucleic acid, whereas in *Staphylococcus aureus,* erythromycin induced resistance to tylosin mediated by $N^6$-dimethylation of adenine. Inducible macrolide-lincosamide-streptogramin resistance in *S.fradiae* NRRL 2702 and *S.hygroscopicus* IFO 12995, which synthesize the macrolides tylosin and maridomycin, respectively, as well as in the lincosamide producer *Streptomyces lincolnensis* NRRL 2936 and the streptogramin type B producer *Streptomyces diastaticus* NRRL 2560. A wide range of different macrolides including chalcomycin, tylosin, and cirramycin induced resistance when tested in an appropriate system. Lincomycin was active as inducer in *S.lincolnensis,* the organism by which it is produced, and streptogramin type B antibiotics induced resistance in *S.fradiae, S.hygroscopicus,* and the streptogramin type B producer *S.diastaticus.* Patterns of adenine methylation found included (i) lincomycin-induced monomethylation in *S.lincolnensis* and constitutive monomethylation in a mutant selected with maridomycin, (ii) concurrent equimolar levels of adenine mono- plus dimethylation in *S.hygroscopicus,* (iii) monomethylation in *S.fradiae* and constitutive dimethylation in a mutant selected with erythromycin, and (iv) adenine dimethylation in *S.diastaticus* induced by ostreogrycin B.

The invention method is not limited to MLS producers exclusively since inducible MLS resistance appears to be widely distributed in Streptomyces, including those not known to produce MLS antibiotics, such as *S.viridochromogenes, Streptomyces rimosus,* and *Streptomyces griseus,* the latter to known to produce oxytetracycline and streptomycin respectively. Insofar as constitutive methylation appears to be linked metabolically to antibiotic production, it may be linked to production of other secondary metabolites as well, and thus the selection procedure described has wider and more general application to strain improvement in *Streptomyces, Micromonospora, Nocardia* and related organisms with inducible ribosomal RNA methylation, with respect to the production of other substances (including polyenes and auermectins) by more efficient fermentation.

It will be apparent to those skilled in the art that a number of modifications and changes may be made without departing from the spirit and scope of the invention. Therefore, it is to be understood that the invention is not to be limited except by the claims which follow:

I claim:

1. A method of increasing the yield of a desired product by an organism selected from Streptomyces, Micromonospora and Nocardia which organism produces that product but which normally must first become inducibly resistant to that product before it can produce the product in maximum yields, which method comprises producing constitutively resistant cells of the organism by supplementing a culture of the organism with an agent in which only cells able to specifically modify the 23S ribosomal RNA constitutively, rather than inducibly, survive thereby producing an organism in which the resistance to the product is expressed without the need for activation by the induction process; followed by purification and utilization of that organism for increased production.

2. A method of increasing the antibiotic yield of an antibiotic producing organism which normally must first become inducibly resistant to the antibiotic which it produces before it can produce the antibiotic in maximum yields, which method comprises producing constitutively resistant cells of the organism by supplementing a culture of the organism with an agent in which only cells able to specifically modify the 23S ribosomal RNA constitutively, rather than inducibly, survive thereby producing an organism in which the resistance to the antibiotic is expressed without the need for activation by the induction process; followed by purification and utilization of that organism that increased antibiotic production.

3. The method of claim 2 in which the antibiotic producing organism is of the Streptomyces family.

4. The method of claim 2 in which the agent with which the culture is supplemented is an agent with low inducing activity.

5. The method of claim 2 in which the antibiotic producing organism is *Streptomyces lincolnensis.*

6. The method of claim 2 in which the antibiotic producing organism is *Streptomyces fradiae.*

7. The method of claim 2 in which the organism is an MLS antibiotic producing organism and the culture is supplemented with a different MLS antibiotic of low inducing activity.

8. The method of claim 2 in which the organism is *Streptomyces lincolnensis* and the agent is maridomycin.

9. The method of claim 2 in which the organism is *Streptomyces fradiae* and the agent is erythromycin.

10. The method of claim 2 in which the organism is of the Streptomyces family and the agent is a noninducing MLS antibiotic other than that produced by the organism.

* * * * *